United States Patent

Pomeranz et al.

[11] Patent Number: 5,201,316
[45] Date of Patent: Apr. 13, 1993

[54] GUIDE WIRE RECEPTACLE FOR CATHETERS HAVING RIGID HOUSINGS

[75] Inventors: Mark L. Pomeranz, Los Gatos; Stephen M. Salmon, Sunnyvale; Pat A. Gingell, San Jose, all of Calif.

[73] Assignee: Cardiovascular Imaging Systems, Inc., Sunnyvale, Calif.

[21] Appl. No.: 672,069

[22] Filed: Mar. 18, 1991

[51] Int. Cl.$^5$ ............................................. A61B 8/12
[52] U.S. Cl. .................................................. 128/662.06
[58] Field of Search ................. 128/662.06, 660.03; 604/99-103

[56] References Cited

U.S. PATENT DOCUMENTS 4,402,684 9/1983 Jessup .
4,748,982 6/1988 Horzewski et al. .
4,762,129 8/1988 Bonzel .
4,794,931 1/1989 Yock .
4,821,731 4/1989 Martinelli et al. .

OTHER PUBLICATIONS

Trimedyne, Inc. brochure, 6 pages entitled "Announcing the Family of 2.5mm Laserprobes".

Primary Examiner—Francis Jaworski
Attorney, Agent, or Firm—Townsend and Townsend

[57] ABSTRACT

An ultrasonic imaging catheter comprises a flexible catheter body having a rigid housing at its distal end. A tapered flexible end piece is secured to the distal end of the rigid housing, and a flexible guide wire tube extends in parallel to both the housing and the flexible end piece from the catheter body. The guide wire tube defines a guide wire lumen capable of receiving a movable guide wire, and the combined structure of the housing, flexible end piece, and flexible guide wire tube minimize constriction of the guide wire as it passes through the guide wire lumen.

21 Claims, 2 Drawing Sheets

GUIDE WIRE RECEPTACLE FOR CATHETERS HAVING RIGID HOUSINGS

The present invention is related to application Ser. No. 07/422,935, filed on Oct. 17, 1989, and now U.S. Pat. No. 5,024,234 the disclosure of which is incorporated herein by reference.

BACKGROUND OF THE INVENTION

1. Field of the Invention

The present invention relates generally to the construction of intravascular catheters. More particularly, the invention relates to intravascular catheters having guide wire receptacles which are compatible with rigid distal housings having ultrasonic imaging components therein.

Arteriosclerosis, also known as atherosclerosis, is a common human ailment arising from the deposition of fatty-like substances, referred to as atheroma or plaque, on the walls of blood vessels. Such deposits occur both in peripheral blood vessels that feed the limbs of the body and coronary blood vessels which feed the heart. When deposits accumulate in localized regions of a blood vessel, blood flow is restricted and the person's health is at serious risk.

Numerous approaches for reducing and removing such vascular deposits have been proposed, including balloon angioplasty where a balloon-tipped catheter is used to dilatate a region of atheroma, atherectomy where a blade or other cutting element is used to sever and remove the atheroma, and laser angioplasty where laser energy is used to ablate at least a portion of the atheroma. In addition to such therapeutic approaches, a variety of techniques for transluminal imaging of atheroma and other diseased regions of a blood vessel have been proposed, including endoscopic imaging techniques and ultrasonic imaging techniques. Common to all such techniques is the use of an intravascular catheter which is positioned at a desired location within the blood vessel to be treated or imaged.

Two alternative approaches may generally be employed to achieve such positioning. In the first approach, the vascular catheter is provided with a "fixed guide wire" secured to its distal end. The fixed guide wire is typically a coiled spring or other elongate resilient member having a preformed, curved tip. The catheter can then be guided through branches within the vascular network by rotating the entire catheter, causing the tip of the guide wire to enter a desired branch as the catheter is moved forward. In the second technique, an entirely separate "movable guide wire" is employed. The movable guide wire is itself a coiled spring or other resilient elongate member and will generally include a curved tip similar to that provided on the fixed guide wires described above. The vascular catheter being positioned includes a guide wire lumen which generally extends down the center of the entire length of the catheter and is sized to receive the movable guide wire. The movable guide wire is first positioned within the vascular system so that its distal end extends beyond the region of interest, and the intravascular catheter is then inserted over the movable guide wire using the guide wire lumen. Such procedures using movable guide wires are commonly referred to as "over-the-wire" insertional techniques.

The use of movable guide wires enjoys a number of advantages over the use of fixed guide wires. In particular, a movable guide wire allows positioning of relatively large diameter catheters which would be difficult to manipulate using a fixed guide wire. The presence of a movable guide wire also facilitates repositioning of the catheter during use and simplifies withdrawal of the catheter and replacement by either the same catheter or a different catheter.

The use of movable guide wires with certain types of intravascular catheters, however, is problematic. Many catheters have internal components within their distal end for imaging or interventional purposes, and such components can interfere with passage of the movable guide wire through the catheter. The use of movable guide wires has been particularly troublesome with imaging catheters of the type employing ultrasonic elements at their distal end, frequently in combination with rotating mirrors. It is undesirable to penetrate the ultrasonic element thus rendering passage of a movable guide wire through the center of the catheter undesirable. Thus, such catheters have normally employed fixed guide wires at their distal ends.

A second consideration in employing movable guide wires relates to their length. In many catheters, the movable guide wire is received in a lumen which extends the entire length of the catheter body. In order to both insert the catheter and remove the catheter while leaving the movable guide wire in place, it is necessary that the movable guide wire have a length equal to at least twice that of the catheter body. In this way, the proximal end of the guide wire may be held in place at all times while the catheter is being inserted or withdrawn. The use of such long guide wires, however, proved highly inconvenient, requiring manipulation of the guide wire in the catheter at great distances from the patient. To overcome these problems, "monorail" systems have been devised for certain types of catheters, including balloon-tipped catheters and laser hot tip catheters.

In such monorail designs, the guide wire lumen extends through only a very short wire lumen formed at the distal end of the catheter. Thus, the length of the guide wire can be reduced to a length which need only be equal to the length of the catheter plus the short length of the wire lumen at the distal end. Such monorail guide wire lumens, however, have not generally been employed in catheters having mechanical and electrical components in their distal end, such as ultrasonic imaging catheters where the passage of a guide wire, even for a short length, is problematic.

The use of such monorail designs with ultrasonic imaging catheters can be particularly problematic. Ultrasonic imaging catheters often require rigid housings, for example to hold the ultrasonic transducer in a fixed spatial relationship with a rotating mirror, and the presence of a rigid housing will frequently bind the passage of the guide wire. Such binding occurs particularly at the junctions between the rigid housing and the proximal and/or distal flexible regions of the catheters. Such flexible regions will often bend at rather sharp angles relative to the rigid housing, and such sharp bends can constrict a guide wire passing through a monorail-type lumen disposed on the side of the housing.

For these reasons, it would be desirable to provide ultrasonic imaging catheters having monorail-type guide wire lumens which are less prone to constricting the passage of a movable guide wire therethrough. In particular, it would be desirable to provide ultrasonic imaging catheters having rigid distal housings where the bending of the catheter is limited in the regions where a rigid housing joins a flexible proximal catheter body and a flexible distal tip of the catheter.

2. Description of the Background Art

U.S. Pat. No. 4,794,931, describes a vascular ultrasonic imaging catheter employing a rotating mirror and/or ultrasonic element to produce a two-dimensional image. The catheter is illustrated to include a fixed guide wire at its distal tip. U.S. Pat. No. 4,762,129, illustrates a balloon dilatation catheter having a laterally-offset lumen extending axially through the balloon and capable of receiving a movable guide wire. U.S. Pat. No. 4,748,982, discloses a balloon dilatation catheter having parallel lumens extending through the catheter body. A side port opens to one of said lumens proximally of the balloon, allowing a movable guide wire to extend from said side port the entire distance to the distal tip of the catheter. U.S. Pat. No. 4,821,731, describes an imaging catheter having a one-dimensional capability. The catheter is introduced over a radially-offset guide wire, but no provisions are made to reduce constriction of the guide wire. U.S. Pat. No. 4,402,684, describes a cannula having a soft tip. Trimedyne, Inc. of Tustin, Calif., sells a hot tip laser catheter having an enlarged metal tip with an axially-offset lumen for receiving a guide wire. The catheter is described in a brochure entitled "*Announcing the Family of 2.5 mm Laserprobes*" dated December 1987.

SUMMARY OF THE INVENTION

According to the present invention, an ultrasonic imaging catheter comprises a rigid housing secured to the distal end of a flexible catheter body. The rigid housing contains ultrasonic imaging components, typically a fixed ultrasonic transducer and a rotatable mirror spaced axially-apart from the transducer for deflecting ultrasonic energy in a desired manner. A flexible tip or end piece is secured to the distal end of the rigid housing, and a flexible guide wire tube extends from the distal end of the flexible catheter body in axial alignment with both the housing and the flexible end piece. The flexible end piece is tapered with a larger diameter proximate the housing and a smaller diameter remote from the housing. In this way, the flexible end piece has a greater stiffness near the junction between it and the housing, with the stiffness gradually lessening in the distal direction away from the housing. Such a stiffness profile helps reduce sharp bending of the guide wire tube at the transition region between the housing and the flexible end piece, thus reducing constriction of a guide wire passing therethrough.

In a preferred embodiment, the flexible end piece is a helical coil having the desired stiffness properties, but flexible polymeric structures may also find use as the end piece. The flexible guide wire tube is preferably a seamless polymeric tube, usually formed from a low friction polymeric material, such as polyethylene. The flexible guide wire tube and flexible end piece are held together by an external sheath which allows a small degree of relative axial movement between the tapered end piece and the flexible guide wire tube. Such relative movement facilitates bending of the distal structure of the structure.

DESCRIPTION OF THE PREFERRED EMBODIMENT

Figure 1:
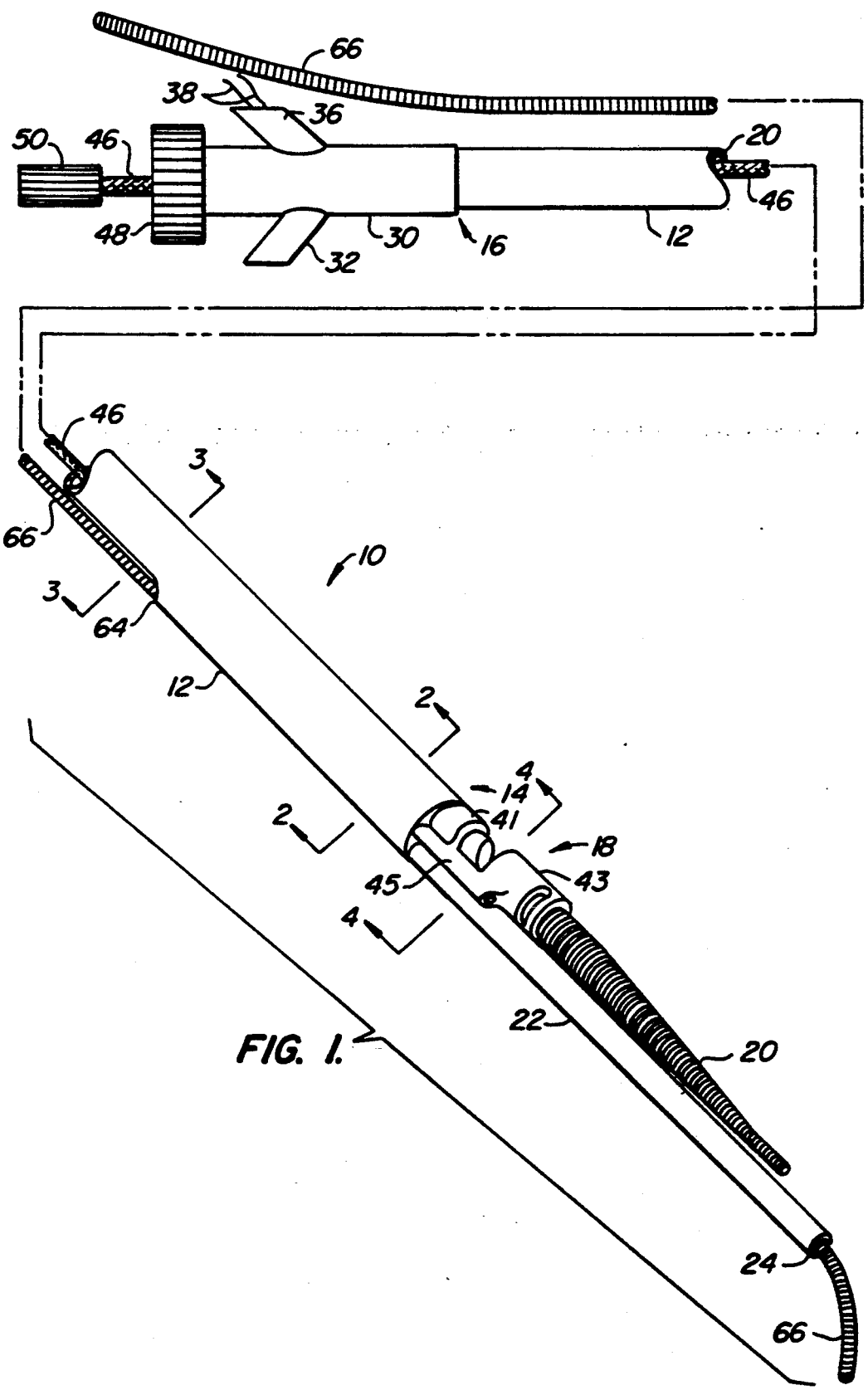
FIG. 1 is a perspective view of an ultrasonic imaging catheter constructed in accordance with the principles of the present invention.
Figure 2:
FIG. 2 is a cross-sectional view of the catheter of FIG. 1, taken along the line 2—2.
Figure 3:
FIG. 3 is a cross-sectional view of the catheter of FIG. 1, taken along line 3—3.
Figure 4:
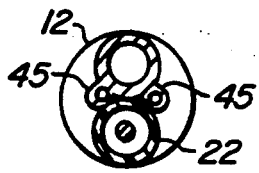
FIG. 4 is a cross-sectional view of the catheter of FIG. 1, taken along line 4—4.

The intravascular catheters of the present invention will include an elongate catheter body which is similar in construction to intravascular catheters of the type which are well known in the art. The catheter body will usually comprise a very flexible tube having proximal and distal ends and at least one lumen extending between said ends. The tube may be formed by extrusion of an organic polymer, typically a thermoplastic, such as nylon, polyurethane, polyethyleneterephthalate (PET), polyvinylchloride (PVC), polyethylene, and the like. The tubes so formed may be reinforced or unreinforced, with reinforcement being provided by metal wires, metal braided cables, or the like. The catheter body will typically have a length from about 60 to 150 cm and a diameter from about 3 to 11 French (F; 0.33 mm). For use in coronary applications, the catheter body will typically have a length from about 120 to 150 cm, and a diameter from about 3 to 6 F, while for peripheral applications, the catheter body will have a length from about 60 to 110 cm and a diameter from about 3 to 11 F.

The housing will be secured to or formed at the distal end of the catheter body. The housing will usually be open, i.e., include one or more apertures, gaps, or the like, which allow for ultrasonic imaging by components located within the interior of the housing. The housing may be formed separately or integrally with the structure of the catheter body. Alternatively, the housing may be closed so long as at least a portion is formed for an ultrasonically-transparent material. In either case, the housing will provide a more rigid structure than the catheter body. Usually, the housing will be very rigid, although a certain degree of flexibility may be desirable in certain applications. The housing will usually be formed from metal, such as stainless steel, or from a rigid plastic, but may also be formed by reinforcement of the catheter body itself within the region intended as the housing. The housing will usually have a cylindrical diameter, having a diameter from about 3 to 11 F, more usually from about 3 to 8 F, although the geometry may vary.

Ultrasonic imaging components within the housing will include an ultrasonic element capable of generating and receiving an ultrasonic imaging signal. Mechanical components will also be provided for sweeping the ultrasonic element in a desired direction, typically a radial sweep as described in U.S. Pat. No. 4,794,931, the disclosure of which is incorporated herein by reference.

The ultrasonic element may be directly rotated or the ultrasonic signal indirectly rotated using a rotatable mirror. Specific systems for providing ultrasonic imaging will be described in connection with the drawings hereinbelow.

The present invention will finds its greatest use with ultrasonic imaging components including a fixed ultrasonic transducer located within a distal region of the rigid housing and a rotatable mirror located within a proximal region of the rigid housing. The mirror is rotated, typically by a drive shaft running through the flexible catheter body, and deflects ultrasonic energy from the transducer in a desired radially-outward path, typically in a circular sweeping pattern. It is very important that the transducer and mirror be held in a rigidly fixed spatial relationship. The requirement for such a rigid housing necessitates that provisions be made for properly incorporating a guide wire lumen in the catheter, as discussed in more detail hereinbelow.

Housing 18 includes a proximal bearing retainer 41 and a distal transducer shield 43 joined by a pair of rigid structural members 45. Such a rigid structure assures that the relative positions of the transducer 40 and rotatable mirror 42 will be precisely maintained, even when the housing is subjected to external bending stresses. Of course, it is not necessary that a pair of structural elements be used, and a single structure element would be sufficient so long as it can maintain the desired rigidity. As illustrated, the structural members 45 are a pair of hollow tubes, but could equally well be rods, or other load bearing elements. Generally, it is desirable for the structural elements 45 to be axially aligned so that they will provide minimum interference with the ultrasonic image being produced.

A flexible end piece will be secured to or formed at the distal end of the rigid housing. The flexible end piece may be substantially solid, substantially hollow, or have an intermediate construction, and will extend beyond the housing by a length of at least 0.3 cm, usually being from about 0.3 to 2.5 cm, more usually being from about 0.5 to 1.5 cm. The end piece will be highly flexible, being more flexible than the catheter housing, and typically being as flexible or nearly flexible as the catheter body. The flexible end piece will usually be formed as a helical coil, but may also be formed from polymers similar to those described in connection with the catheter body. The end will usually be formed separately from the housing and the catheter body, but integral constructions where at least a portion of the flexible tip is formed continuously with the housing and/or the catheter body may also find use.

The flexible end piece will have a tapered profile with a diameter at the proximal end generally equal to or slightly smaller than that of the housing. The diameter of the end piece will decrease in the distal direction, and will usually have a diameter below about 0.5 mm, typically being below about 0.4 mm, at its distal tip. The tapering will generally be smooth, although it does not have to be entirely uniform, and in the illustrated embodiment there is a small cylindrical section in the end piece at its distal end.

The tapered profile of the end piece provides a desired decrease in bending stiffness along its length in the distal direction. That is, the end piece will generally have a somewhat greater stiffness at its proximal end (where the diameter is greater) and a lesser stiffness at the distal end (where the diameter is less). Generally, the bending stiffness of the flexible end piece will be in the range from about 0.03 in-lb-in to about 0.5 in-lb-in, usually being in the range from about 0.05 in-lb-in to about 0.4 in-lb-in. The bending stiffness at the proximal end will usually be at the higher end of such ranges, while the bending stiffness at the distal end will usually be at the lower end of such ranges.

As used herein and in the claims, bending stiffness constant ($K_B$) is defined as $$K_B = RFd,$$

where
R = bending radius (in.);
F = deflection force (lb.); and
d = length of flexible end piece (in.).

The bending stiffness constant may be measured using a conventional 3-point compression tester, such as the Instron Tensile Compression Tester. The flexible end piece is placed on a pair of supports spaced apart by a known length (L). A deflection force ($F_d$) is applied to the flexible end piece at a location midway between the supports on the resulting deflection measured. The bending radius (R) can then be determined from the measured deflection. Alternatively, the radius can be determined by graphical analysis. In either case, the bending stiffness constant ($K_B$) can then be calculated using the above formula.

A flexible guide wire tube will be provided in a parallel or "monorail" configuration at the distal end of the catheter body. That is, the flexible guide wire tube will be parallel to and axially-aligned with both the rigid housing and the flexible end piece to provide a lumen for receiving a conventional movable guide wire. Usually, the flexible guide wire tube will be concentrically aligned with a guide wire lumen formed in the flexible catheter body to provide a continuous lumen over a desired length at the distal end of the catheter, typically in the range from about 1 cm to about 5 cm, usually in the range from about 2 cm to about 4 cm. Alternatively, the guide wire tube may extend for a preselected length in parallel to the catheter body so that the tube provides the entire length of the "monorail."

The flexible guide wire tube is preferably formed as a seamless polymeric tube, typically from a low friction polymer material, such as polyethylene. The flexible guide wire tube is usually joined at its proximal end to the distal end of the catheter body and is held together with the housing and flexible end piece by an external sheath, typically formed from a heat-shrinkable polymer, such as polyethylene. Usually, the flexible guide wire tube will be otherwise unconnected to the housing and the flexible end piece. Thus, due to the elastic nature of the flexible sheath, the flexible guide wire tube will be able to axially move relative to both the housing and the flexible end piece. Such movement facilitates bending of the overall structure as the catheter is introduced around tight bends in the vascular system.

Referring now to FIGS. 1–6, the construction of an ultrasonic imaging catheter in accordance with the principles of the present invention will be described in detail. A catheter 10 includes a catheter body 12 having a distal end 14 and a proximal end 16. A rigid housing 18 is secured to the distal end 14 of catheter body 12, and tapered flexible end piece 20 secured to a distal end of the housing 18. A flexible guide wire tube 22 is also secured to the distal end 14 of catheter body 12 and extends from said distal end in parallel to both the housing 18 and the flexible end piece 20, terminating in a distal tip 24 which is spaced distally from the distal end of the flexible end piece.

A proximal housing 30 is secured to the proximal end 16 of catheter body 12 and includes a first access port 32 which is connected to a central lumen 34 in the catheter body and a second access port 36 which provides entry for a pair of wires 38 which are ultimately connected to a transducer element 40 within the rigid housing 18.

A rotatable mirror 42 is mounted on a bearing member 44 which in turn is connected to a drive shaft 46 extending through the central lumen 34 of the catheter body 12. The drive shaft 46 passes through a fitting 48 at the proximal end of proximal housing 30 and terminates in a spindle 50 which may be driven by a conventional motor drive unit for rotating mirror to produce the desired ultrasonic image. Such motor drive units, as well as the circuitry for producing the image are now well known in the art and are amply described in both the patent and medical literature.

The flexible guide wire tube 22 defines a lumen 60 which is coaxially aligned with a guide wire lumen 62 formed in the flexible catheter body 12. The guide wire lumen 62 extends from the distal end 14 of the catheter body in the proximal direction and terminates at a peripheral port 64 located from about 10 cm to 30 cm from the distal end 14. In this way, the conventional movable guide wire 66 may be introduced through the contiguous lumens 60 and 62 in a conventional "monorail" fashion, as illustrated in FIG. 1. The advantages of such a monorail configuration are described hereinabove.

Figure 7:
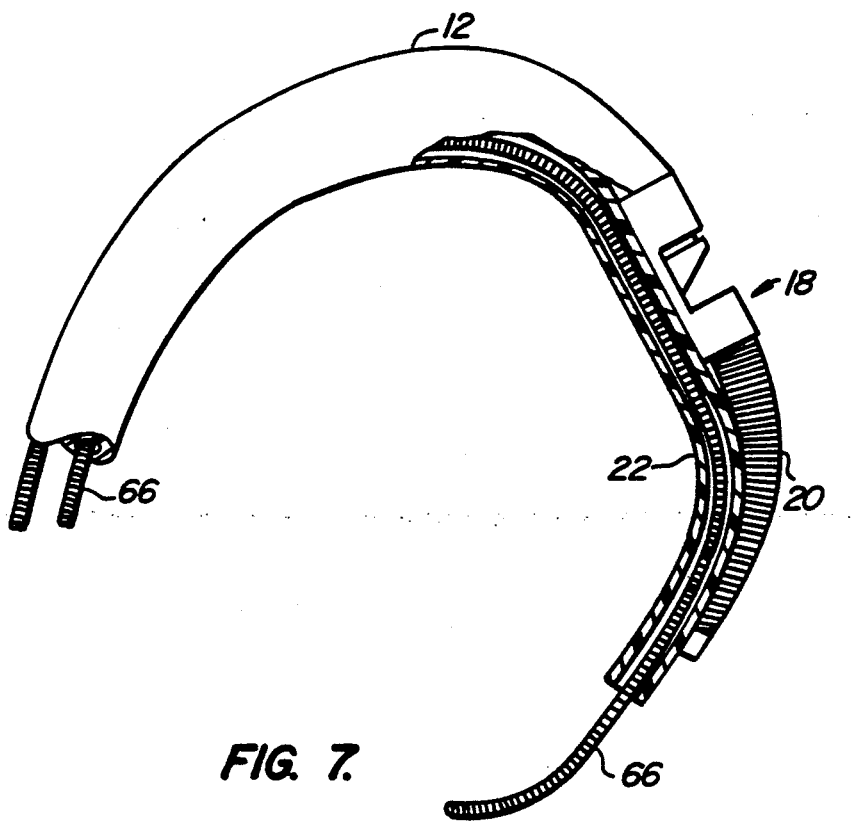
FIG. 7 illustrates the distal end of the catheter of FIG. 1 in a tightly curved configuration.
Figure 5:
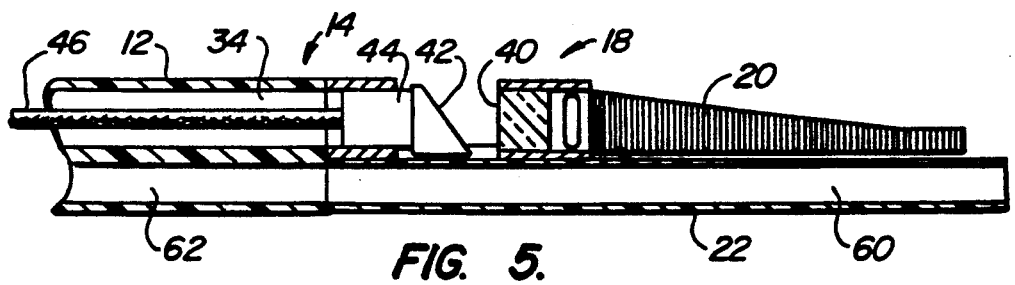
FIG. 5 is a detailed view of the distal end of the catheter of FIG. 1, shown in cross-section.
Figure 6:
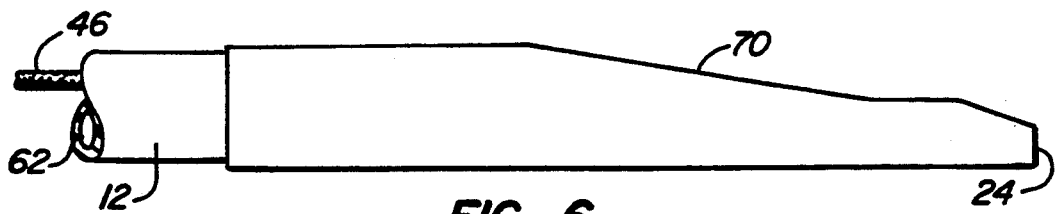
FIG. 6 is a detailed view of the distal end of the catheter of FIG. 5, shown with the external sheath in place.

The flexible guide wire tube 22 will be held together with both the housing 18 and the flexible end piece 20 using an external sheath 70 (FIG. 6). The sheath 70 will be formed from an acoustically transparent material, such as heat shrinkable polyethylene, which is formed over the distal end of the catheter 10 in a conventional manner. The sheath 70 will be sufficiently elastic to allow the guide wire tube 60 to slide or slip by the housing 18 and flexible end piece 20 as the catheter 10 is bent, as illustrated in FIG. 7. It can be seen in FIG. 7 that the flexible guide wire tube 22 is able to provide a relatively smooth curve for passage of the movable guide wire 66, even though the housing 18 remains rigid and unbent. In particular, it can be seen that bending in the region of the junction between housing 18 and flexible end piece 20 is relatively minor, while a controlled bending is provided over the more distal portion of the end piece. Such controlled bending helps eliminate constriction of the guide wire 66 as it passes by the rigid housing 18.

Figure 8:
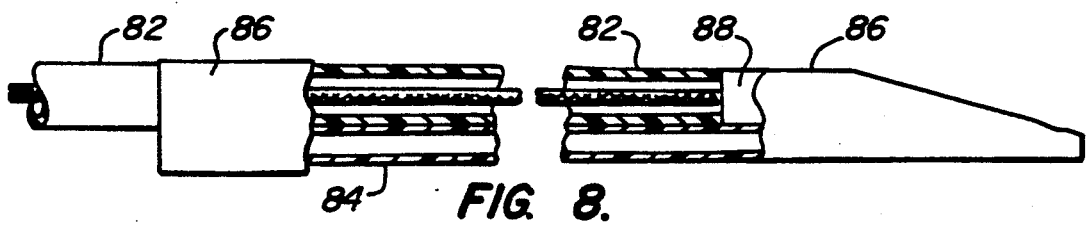
FIG. 8 is a detailed view of the distal end of an alternative embodiment of a catheter constructed in accordance with the principles of the present invention, shown with portions broken away.

FIG. 8 illustrates an alternate embodiment 80 of the catheter of the present invention. The catheter 80 is generally the same as that illustrated in FIGS. 1-6, except that the catheter body 82 does not include a guide wire lumen. Instead, a guide wire tube 84 extends past the flexible end piece (hidden by sheath 86), housing 88, as well as past a preselected distal length of the catheter body 82 (corresponding to the length of lumen 62 described above). The sheath 86 extends sufficiently far in the proximal direction to join the tube 84 to the catheter body 82.

Although the foregoing invention has been described in detail for purposes of clarity of understanding, it will be obvious that certain modifications may be practiced within the scope of the appended claims.

What is claimed is:

1. An ultrasonic imaging catheter comprising:
    a flexible catheter body having a proximal end and a distal end;
    a rigid housing secured to the distal end of the flexible catheter body, said housing including a distal portion and a proximal portion joined by an external metal rod;
    a flexible end piece having a tapered distal end and a proximal end secured to the housing, whereby the stiffness of the end piece lessens in the distal direction away form the housing;
    means within the housing for forming an ultrasonic image in a plane normal to the housing, whereby the metal rod forms an image artifact; and
    a flexible guide wire tube axially-aligned with but separate from the housing and the flexible end piece and having a continuous lumen extending proximally form the distal tip of the end piece to beyond the proximal end of the housing, whereby the flexible guide wire tube may slip relative to the flexible end piece when the tube and end piece are bent.

2. An ultrasonic imaging catheter as in claim 1, wherein the rigid housing is formed form stainless steel.

3. An ultrasonic imaging catheter as in claim 1, wherein the proximal and distal portions of the rigid cylindrical housing are joined by at least two external metal rods.

4. An ultrasonic imaging catheter as in claim 1, wherein the flexible end piece is a helical coil.

5. An ultrasonic imaging catheter as in claim 1, wherein the flexible end piece is composed of an elastomeric polymer.

6. An ultrasonic imaging catheter as in claim 1, wherein the flexible guide wire tube is composed of a polymer.

7. An ultrasonic imaging catheter as in claim 6, wherein the flexible guide wire tube is a seamless polymeric tube.

8. An ultrasonic imaging catheter comprising:
    a flexible catheter body having a proximal end, a distal end, a central lumen, and a guide wire lumen;
    a rigid housing secured to the distal end of the flexible catheter body and aligned with the central lumen thereof, said housing including a proximal bearing retainer, a distal transducer shield, and an axially-aligned structural members rigidly joining the retainer to the shield;
    a flexible end piece having a tapered distal end and a proximal end secured to the distal transducer shield, wherein the flexible end piece has a bending stiffness constant in the range from about 0.05 to 0.4 in-lb-in with a higher constant near the proximal end thereof and a lower constant near the distal end thereof;
    a flexible guide wire tube axially-aligned with the housing and flexible end piece and having a lumen which is joined contiguously with the guide wire lumen in the catheter body;
    a rotatable mirror in the bearing retainer;
    means in the central lumen for rotating the rotatable mirror;
    an ultrasonic transducer in the transducer shield; and
    an ultrasonically transparent sheath formed over the housing, end piece, and guide wire tube, whereby the guide wire tube retains freedom of movement relative to the end piece.

9. An ultrasonic imaging catheter as in claim 8, wherein the guide wire lumen in the catheter body extends over only a portion of said body.

10. An ultrasonic imaging catheter as in claim 9, wherein the catheter body has a length from about 65 cm to 150 cm and the guide wire lumen has a length from about 10 cm to 30 cm.

11. An ultrasonic imaging catheter as in claim 8, wherein the rigid housing is formed from stainless steel.

12. An ultrasonic imaging catheter as in claim 8, wherein the flexible end piece is a helical coil.

13. An ultrasonic imaging catheter as in claim 8, wherein the flexible end piece is composed of a polymer.

14. An ultrasonic imaging catheter as in claim 8, wherein the flexible guide wire tube is composed of a polymer.

15. An ultrasonic imaging catheter as in claim 14, wherein the flexible guide wire tube is a seamless polymeric tube.

16. An ultrasonic imaging catheter as in claim 8, wherein the bearing retainer and transducer shield are joined by at least two axially-aligned structural members.

17. An improved ultrasonic imaging catheter of the type comprising a catheter body having a housing at its distal end, a fixed ultrasonic transducer disposed within the housing, and a rotatable mirror axially spaced-apart form the transducer within the housing and disposed to reflect and receive ultrasonic energy about the periphery of the housing, wherein the improvement comprises:

a flexible end piece having a proximal end and a distal end, wherein the proximal end is secured to the housing and the end piece is tapered in the direction from the proximal end to the distal end, whereby the stiffness of the end piece lessens in the distal direction away from the housing; and a flexible guide wire tube attached to the outside of the housing and the end piece nd having a continuous lumen extending proximally form the distal tip of the end piece to at least the proximal end of the housing wherein the tub is able to slide relative to the end piece as the end piece is bent.

18. An ultrasonic imaging catheter as in claim 17, wherein the flexible end piece is a helical coil.

19. An ultrasonic imaging catheter as in claim 17, wherein the flexible end piece is composed of a polymer.

20. An ultrasonic imaging catheter as in claim 17, wherein the flexible guide wire tube is composed of a polymer.

21. An ultrasonic imaging catheter as in claim 20, wherein the flexible guide wire tube is a seamless polymeric tube.

* * * * *